US009113846B2

(12) United States Patent
Zinaty et al.

(10) Patent No.: US 9,113,846 B2
(45) Date of Patent: Aug. 25, 2015

(54) IN-VIVO IMAGING DEVICE PROVIDING DATA COMPRESSION

(75) Inventors: Ofra Zinaty, Haifa (IL); Eli Horn, Kiryat Motzkin (IL); Ido Bettesh, Zichron Yaakov (IL)

(73) Assignee: GIVEN IMAGING LTD., Yoqneam Ilite (IL)

( * ) Notice: Subject to any disclaimer, the term of this patent is extended or adjusted under 35 U.S.C. 154(b) by 1679 days.

(21) Appl. No.: 10/991,098

(22) Filed: Nov. 18, 2004

(65) Prior Publication Data

US 2005/0159643 A1 Jul. 21, 2005

Related U.S. Application Data

(63) Continuation-in-part of application No. 10/202,626, filed on Jul. 25, 2002, now abandoned.

(60) Provisional application No. 60/307,605, filed on Jul. 26, 2001.

(51) Int. Cl.

| | |
|---|---|
| ***H04N 7/12*** | (2006.01) |
| ***H04N 11/02*** | (2006.01) |
| ***H04N 11/04*** | (2006.01) |
| ***A61B 5/00*** | (2006.01) |
| ***A61B 1/04*** | (2006.01) |
| ***H04N 5/225*** | (2006.01) |
| ***H04N 7/18*** | (2006.01) |
| ***H04N 19/60*** | (2014.01) |
| *A61B 1/00* | (2006.01) |

(52) U.S. Cl.
CPC ............... *A61B 5/7232* (2013.01); *A61B 1/041* (2013.01); *A61B 1/042* (2013.01); *H04N 5/2252* (2013.01); *H04N 7/185* (2013.01); *H04N 19/60* (2013.01); *A61B 1/00016* (2013.01)

(58) Field of Classification Search
CPC ..... A61B 1/00016; A61B 1/041; A61B 1/042
USPC ................. 375/240.01, E7.266; 348/E5.026, 348/E7.088
See application file for complete search history.

(56) References Cited

U.S. PATENT DOCUMENTS

| | | | |
|---|---|---|---|
| 3,971,362 | A | 7/1976 | Pope et al. |
| 3,984,628 | A | 10/1976 | Sharp |
| 4,243,652 | A | 1/1981 | Francis |
| 4,273,431 | A | 6/1981 | Farmer et al. |

(Continued)

FOREIGN PATENT DOCUMENTS

| | | |
|---|---|---|
| DE | 34 40 177 | 5/1986 |
| JP | S47-4376 | 2/1972 |

(Continued)

OTHER PUBLICATIONS

Japanese Office Action of Application No. 2003-516219 mailed on Aug. 12, 2008.
Korean Office Action of Application No. 10-2004-7001173 mailed on Nov. 26, 2008.
International Search Report for PCT/IL2004/000287 dated Mar. 16, 2005.

(Continued)

*Primary Examiner* — Nhon Diep
(74) *Attorney, Agent, or Firm* — Pearl Cohen Zedek Latzer Baratz LLP

(57) ABSTRACT

A device, system and method may enable the obtaining of in vivo images from within body lumens or cavities, such as images of the gastrointestinal (GI) tract, where the data such as mosaic image data may be transmitted or otherwise sent to a receiving system in a compressed format.

14 Claims, 7 Drawing Sheets

(56) References Cited

U.S. PATENT DOCUMENTS 4,278,077 A 7/1981 Mizumoto
4,310,228 A 1/1982 Terada
4,323,916 A 4/1982 Dischert et al.
4,428,005 A 1/1984 Kubo
4,532,918 A 8/1985 Wheeler
4,539,603 A 9/1985 Takeuchi et al.
4,631,582 A 12/1986 Nagasaki
4,642,678 A 2/1987 Cok
4,646,724 A 3/1987 Sato et al.
4,668,860 A 5/1987 Anthon
4,689,621 A 8/1987 Kleinberg
4,689,689 A * 8/1987 Saito et al. .................... 348/366
4,698,664 A 10/1987 Nichols et al.
4,786,982 A 11/1988 Wakahara et al.
4,834,070 A 5/1989 Saitou
4,841,291 A 6/1989 Swix et al.
4,844,076 A 7/1989 Lesho et al.
4,936,823 A 6/1990 Colvin
5,032,913 A 7/1991 Hattori et al.
5,042,494 A 8/1991 Alfano
5,126,842 A 6/1992 Andrews et al.
5,187,572 A 2/1993 Nakamura et al.
5,202,961 A 4/1993 Mills et al.
5,209,220 A 5/1993 Hiyama et al.
5,241,170 A 8/1993 Field
5,279,607 A 1/1994 Schentag et al.
5,319,471 A * 6/1994 Takei et al. .................... 358/451
5,351,161 A 9/1994 MacKay et al.
5,355,450 A 10/1994 Garmon et al.
5,373,322 A 12/1994 Laroche
5,381,784 A 1/1995 Adair
5,382,976 A 1/1995 Hibbard
5,406,938 A 4/1995 Mersch et al.
5,418,565 A 5/1995 Smith
5,467,413 A 11/1995 Barrett
5,486,861 A 1/1996 Miyamoto et al.
5,493,335 A 2/1996 Parulski et al.
5,506,619 A 4/1996 Adams
5,519,828 A 5/1996 Rayner
5,523,786 A 6/1996 Parulski
5,594,497 A 1/1997 Ahem et al.
5,603,687 A 2/1997 Hori et al.
5,604,531 A 2/1997 Iddan et al.
5,629,734 A 5/1997 Hamilton
5,643,175 A 7/1997 Adair
5,652,621 A 7/1997 Adams
5,678,568 A 10/1997 Uchikubo et al.
5,697,384 A 12/1997 Miyawaki
5,697,885 A 12/1997 Konomura et al.
5,730,702 A 3/1998 Tanaka et al.
5,751,340 A * 5/1998 Strobl et al. .................... 348/65
5,798,846 A * 8/1998 Tretter .......................... 382/262
5,812,187 A 9/1998 Watanabe
5,819,736 A 10/1998 Avny et al.
5,819,740 A 10/1998 Muhlenberg
5,827,190 A 10/1998 Palcic et al.
5,830,141 A 11/1998 Makram-Ebeid et al.
5,833,603 A 11/1998 Kovacs et al.
5,875,280 A 2/1999 Takaiwa et al.
5,908,294 A 6/1999 Schick et al.
5,929,901 A 7/1999 Adair et al.
5,956,467 A * 9/1999 Rabbani et al. ................ 358/1.9
5,987,179 A 11/1999 Riek et al.
5,993,378 A 11/1999 Lemelson
5,999,662 A 12/1999 Burt et al.
6,014,727 A 1/2000 Creemer
6,054,943 A 4/2000 Lawrence
6,088,606 A 7/2000 Ignotz et al.
6,095,989 A 8/2000 Hay et al.
6,124,888 A 9/2000 Terada et al.
6,125,201 A * 9/2000 Zador .......................... 382/166
6,167,084 A 12/2000 Wang et al.
6,173,317 B1 1/2001 Chaddha et al.
6,175,757 B1 1/2001 Watkins
6,177,984 B1 1/2001 Jacques
6,184,922 B1 2/2001 Saito et al.
6,208,354 B1 3/2001 Porter
6,229,578 B1 5/2001 Acharya et al.
6,233,476 B1 5/2001 Strommer
6,240,312 B1 5/2001 Alfano et al.
6,266,454 B1 * 7/2001 Kondo .......................... 382/300
6,289,165 B1 9/2001 Abecassis
6,304,284 B1 10/2001 Dunton et al.
6,310,642 B1 10/2001 Adair et al.
6,314,211 B1 11/2001 Kim et al.
6,328,212 B1 12/2001 Metlitasky et al.
6,351,606 B1 2/2002 Yamakazi
6,356,276 B1 * 3/2002 Acharya ....................... 345/600
6,364,829 B1 4/2002 Fulgham
6,389,176 B1 * 5/2002 Hsu et al. ...................... 382/254
6,414,996 B1 7/2002 Owen et al.
6,452,633 B1 * 9/2002 Merrill et al. ................. 348/302
6,492,982 B1 12/2002 Matsuzaki et al.
6,498,948 B1 12/2002 Ozawa et al.
6,501,862 B1 12/2002 Fukuhara et al.
6,504,990 B1 1/2003 Abecassis
6,560,309 B1 5/2003 Becker et al.
6,600,517 B1 7/2003 He et al.
6,607,301 B1 8/2003 Glukhovsky et al.
6,636,263 B2 10/2003 Oda
6,661,463 B1 12/2003 Geshwind
6,667,765 B1 12/2003 Tanaka
6,690,412 B1 2/2004 Higo
6,697,109 B1 2/2004 Daly
6,697,540 B1 2/2004 Chen
6,709,387 B1 3/2004 Glukhovsky et al.
6,772,003 B2 8/2004 Kaneko et al.
6,847,392 B1 1/2005 House
6,847,736 B2 * 1/2005 Itokawa ........................ 382/240
6,865,718 B2 3/2005 Montalcini
6,904,308 B2 6/2005 Frisch et al.
6,937,291 B1 8/2005 Gryskiewicz
6,939,290 B2 9/2005 Iddan
6,944,316 B2 9/2005 Glukhovsky et al.
6,950,690 B1 9/2005 Meron
6,972,791 B1 12/2005 Yomeyama
6,976,229 B1 12/2005 Balabanovic
7,009,634 B2 3/2006 Iddan et al.
7,039,453 B2 5/2006 Mullick et al.
7,044,908 B1 5/2006 Montalbo et al.
7,057,664 B2 6/2006 Law et al.
7,116,352 B2 10/2006 Yaron
7,209,170 B2 4/2007 Nishino et al.
7,236,191 B2 * 6/2007 Kalevo et al. .............. 348/222.1
7,319,781 B2 1/2008 Chen et al.
7,486,981 B2 2/2009 Davidson
7,495,993 B2 2/2009 Wang
7,505,062 B2 3/2009 Davidson et al.
2001/0017649 A1 8/2001 Yaron
2001/0019364 A1 9/2001 Kawahara
2001/0035902 A1 11/2001 Iddan et al.
2002/0042562 A1 4/2002 Meron et al.
2002/0054290 A1 5/2002 Vurens
2002/0068853 A1 6/2002 Adler
2002/0087047 A1 7/2002 Remijan
2002/0093484 A1 7/2002 Skala et al.
2002/0103417 A1 8/2002 Gazdzinski
2002/0109774 A1 8/2002 Meron et al.
2002/0171669 A1 11/2002 Meron et al.
2002/0173718 A1 11/2002 Frisch et al.
2002/0177779 A1 11/2002 Adler et al.
2002/0193664 A1 12/2002 Ross et al.
2002/0198439 A1 12/2002 Mizuno
2003/0020810 A1 1/2003 Takizawa et al.
2003/0023150 A1 1/2003 Yokoi et al.
2003/0043263 A1 3/2003 Glukhovsky et al.
2003/0060734 A1 3/2003 Yokoi et al.
2003/0085994 A1 5/2003 Fujita et al.
2003/0117491 A1 6/2003 Avni et al.
2003/0139661 A1 7/2003 Kimchy et al.
2003/0151661 A1 8/2003 Davidson
2003/0156188 A1 8/2003 Abrams, Jr.
2003/0158503 A1 8/2003 Matsumoto
2003/0167000 A1 9/2003 Mullick

(56) References Cited

U.S. PATENT DOCUMENTS

| | | | |
|---|---|---|---|
| 2003/0174208 | A1 | 9/2003 | Glukhovsky et al. |
| 2003/0181788 | A1 | 9/2003 | Yokoi et al. |
| 2003/0208107 | A1 | 11/2003 | Refael |
| 2003/0213495 | A1 | 11/2003 | Fujita et al. |
| 2003/0216670 | A1 | 11/2003 | Beggs |
| 2003/0229268 | A1 | 12/2003 | Uchiyama et al. |
| 2004/0027500 | A1 | 2/2004 | Davidson et al. |
| 2004/0111031 | A1 | 6/2004 | Alfano et al. |
| 2004/0215059 | A1 | 10/2004 | Homan et al. |
| 2004/0225190 | A1 | 11/2004 | Kimoto et al. |
| 2004/0225223 | A1 | 11/2004 | Honda et al. |
| 2004/0242962 | A1 | 12/2004 | Uchiyama |
| 2004/0249274 | A1 | 12/2004 | Yaroslavsky |
| 2004/0249291 | A1 | 12/2004 | Honda et al. |
| 2005/0038321 | A1 | 2/2005 | Fujita |
| 2005/0159643 | A1 | 7/2005 | Zinaty et al. |
| 2005/0165279 | A1 | 7/2005 | Adler et al. |
| 2005/0182295 | A1 | 8/2005 | Soper et al. |
| 2005/0283065 | A1 | 12/2005 | Babayoff |
| 2006/0082648 | A1 | 4/2006 | Iddan et al. |
| 2006/0158512 | A1 | 7/2006 | Iddan et al. |
| 2006/0164511 | A1 | 7/2006 | Krupnik |
| 2006/0195014 | A1 | 8/2006 | Seibel et al. |

FOREIGN PATENT DOCUMENTS

| | | | |
|---|---|---|---|
| JP | S47-41473 | | 12/1972 |
| JP | S 55-121779 | | 9/1980 |
| JP | S 57-45833 | | 3/1982 |
| JP | S 63-70820 | | 3/1988 |
| JP | S 63-226615 | | 9/1988 |
| JP | 03-220865 | A | 9/1991 |
| JP | 4109927 | | 4/1992 |
| JP | 1992-144533 | | 5/1992 |
| JP | 5015515 | | 1/1993 |
| JP | 6-038201 | | 2/1994 |
| JP | 07-274164 | A | 10/1995 |
| JP | 7-275200 | | 10/1995 |
| JP | 09-037243 | A | 2/1997 |
| JP | H 10-65131 | | 3/1998 |
| JP | 10-134187 | A | 5/1998 |
| JP | 11-211997 | | 8/1999 |
| JP | H 11-290269 | | 10/1999 |
| JP | 2000-278693 | | 10/2000 |
| JP | 2000-295667 | | 10/2000 |
| JP | 2000-324513 | A | 11/2000 |
| JP | 2000/358242 | | 12/2000 |
| JP | 2001-025004 | | 1/2001 |
| JP | 2001-028709 | A | 1/2001 |
| JP | 20010017649 | | 1/2001 |
| JP | 2001-112740 | | 4/2001 |
| JP | 2001-170002 | | 6/2001 |
| JP | 2001-298366 | | 10/2001 |
| JP | 2001-299692 | A | 10/2001 |
| JP | 2002-165227 | | 6/2002 |
| JP | 2002-247365 | A | 8/2002 |
| JP | 2002-290744 | A | 10/2002 |
| JP | 2002-320235 | | 10/2002 |
| JP | 2002-369142 | | 12/2002 |
| JP | 2003-038424 | A | 2/2003 |
| JP | 2004536644 | | 2/2003 |
| JP | 2003/070728 | | 3/2003 |
| JP | 2004-153744 | | 5/2004 |
| JP | 2004-167163 | | 6/2004 |
| JP | 2004-326991 | | 11/2004 |
| JP | 2005026807 | | 1/2005 |
| JP | 2005-143668 | | 6/2005 |
| JP | 2005-156217 | | 6/2005 |
| JP | 2006-140642 | | 6/2006 |
| JP | 2008-079746 | | 4/2008 |
| WO | WO 97/33513 | | 9/1997 |
| WO | WO 99/40587 | | 8/1999 |
| WO | WO 99/60353 | | 11/1999 |
| WO | WO 00/22975 | | 4/2000 |
| WO | WO 00/76391 | | 12/2000 |
| WO | WO 01/06926 | | 2/2001 |
| WO | WO 01/35813 | | 5/2001 |
| WO | WO 01/50180 | | 7/2001 |
| WO | WO 01/50941 | | 7/2001 |
| WO | WO 01/65995 | | 9/2001 |
| WO | WO 01/87377 | | 11/2001 |
| WO | WO 02/054932 | | 7/2002 |
| WO | WO 02/080753 | | 10/2002 |
| WO | WO 03/009739 | | 2/2003 |
| WO | WO 03/010967 | | 2/2003 |
| WO | WO03010967 | | 2/2003 |
| WO | WO 2004/082472 | | 9/2004 |
| WO | WO 2004/088448 | | 10/2004 |
| WO | WO 2005/062715 | | 7/2005 |

OTHER PUBLICATIONS

International Search Report for PCT/IL02/00621 dated Dec. 6 2002.

The Radio Pill, Rowlands, et al , British Communications and Electronics, Aug. 1960, pp. 598-601.

Wellesley company sends body montiors into space—Crum, Apr. 1998.

Wireless transmission of a color television moving image from the stomach using a miniature CCD camera. light source and microwave transmitter Swain CP, Gong F, Mills TN Gastrointest Endosc 1997;45:AB40.

BBC News Online—Pill camera to ‘broadcast from the gut’, Feb. 21, 2000, www news bbc co uk.

Biomedical Telemetry, R Stewart McKay, published by John Wiley and Sons, 1970.

Office Action for U.S. Appl. No. 11/087,606 mailed on Aug. 28, 2009.

Office Action for U.S. Appl. No. 11/087,606 mailed Jul. 12, 2013.

Office Action for Japanese Patent Application No. 2006-507593 dated Jun. 28, 2011.

Keren et al., “Restoring Subsampled Color Images”, Machine Vision and Applications, vol. 11, pp. 197-202, 1999.

Liao et al., “Interpolation Filter Architecture for Subsampled Image”, Consumer Electronics, Digest of Technical Papers, International Conference on Rosemont, pp. 376-377, Jun. 2-4, 1992.

Supplementary European Search Report for European Application No. 04 72 4102 mailed on Mar. 3, 2010.

Japanese Office Action for Japanese Patent Application No. 2008-502556 mailed Oct. 18, 2011.

Office Action for Japanese Patent Application No. 2006-507593 dated Mar. 31, 2010.

Office Action for U.S. Appl. No. 11/087,606 mailed on Mar. 31, 2009.

Office Action for U.S. Appl. No. 10/551,436 mailed Mar. 3, 2009.

Final Office Action for U.S. Appl. No. 10/551,436 mailed Aug. 4, 2008.

Office Action for U.S. Appl. No. 10/551,436 mailed Feb. 22, 2008.

Final Office Action for U.S. Appl. No. 10/551,436 mailed Sep. 12, 2007.

Office Action for U.S. Appl. No. 10/551,436 mailed Mar. 13, 2007.

Video Camera to “TAKE”—RF System Lab, Dec. 25, 2001.

“Synchronized nQUAD Technology” www.cartesiantech.com, 1998-2000.

Yang et al., “Two Image Photometric Stereo Method”, SPIE, vol. 1826, Intelligent Robots and Computer Vision XI, 1992.

www.dynapel.com, Motion Perfect® product literature, printed Jul. 22, 2003.

www.zdnet.co.uk/pcmag/trends/2001/04/06.html, “Perfect motion on the Net”—Cliff Joseph, printed Dec. 25, 2001.

Muresan, D.D. and T.W. Parks, “Optimal recovery approach to image interpolation”, IEEE Proc. ICIP., vol. 3, 2001, pp. 7-10.

Gunturk, B. et al., “Color plane interpolation using alternating projections,” IEEE Transactions on Image Processing, vol. 11, 2002, pp. 997-1013.

Kimmel, “Demosaicing: Image reconstruction from color ccd samples”, IEEE Transactions onImage Processing, vol. 8, 1999, pp. 1221-1228.

Office Action for corresponding U.S. Appl. No. 11/087,606, mailed Mar. 24, 2015.

* cited by examiner $$\begin{bmatrix} Y \\ C_r \\ C_b \\ G_{diff} \end{bmatrix} = \begin{bmatrix} 0.25 & 0.25 & 0.25 & 0.25 \\ 0.75 & -0.25 & -0.25 & -0.25 \\ -0.25 & -0.25 & -0.25 & 0.75 \\ 0 & 1 & -1 & 0 \end{bmatrix} \begin{bmatrix} R \\ G_1 \\ G_2 \\ B \end{bmatrix}$$

Fig. 4

IN-VIVO IMAGING DEVICE PROVIDING DATA COMPRESSION

CROSS-REFERENCE TO RELATED APPLICATION

This application is a continuation-in-part of U.S. patent application Ser. No. 10/202,626, filed Jul. 25, 2002 now abandoned, entitled "Diagnostic Device Using Data Compression", which in turn claims benefit from prior provisional application No. 60/307,605 entitled "Imaging Device Using Data Compression" and filed on Jul. 26, 2001 each of which are incorporated by reference herein in their entirety.

FIELD OF THE INVENTION

The present invention relates to an in-vivo device, system, and method such as for imaging the digestive tract; more specifically, to an in-vivo device, system, and method where information transmitted or sent may be compressed.

BACKGROUND OF THE INVENTION

Devices, systems, and methods for performing in-vivo imaging, for example, of passages or cavities within a body, and for gathering information other than or in addition to image information (e.g. temperature information, pressure information, etc.), are known in the art. Such devices may include, inter alia, various endoscopic imaging systems and various autonomous imaging devices for performing imaging in various internal body cavities.

An in-vivo imaging device may, for example, obtain images from inside a body cavity or lumen, such as the gastrointestinal (GI) tract. Such an imaging device may include, for example, an illumination unit, such as a plurality of light emitting diodes (LEDs) or-other suitable light sources, an imager, and an optical system, which may focus images onto the imager. A transmitter and antenna may be included for transmitting the image and/or other data signals. An external receiver/recorder, for example, worn by the patient, may record and store images and other data Images and other data may be displayed and/or analyzed on a computer or workstation after downloading the data recorded. The number and size of image data per frame and/or other data to be transmitted may be limited by the time period, power, and/or bandwidth that may be required to transmit each image frame and/or other data. Transmission may be wireless, for example, by RF communication or via wire.

Methods for compressing image or video data may be known, for example, compression algorithms such as JPEG and MPEG may be used to compress image and video data.

SUMMARY OF THE INVENTION

An embodiment of the device, system and method of the present invention enables the obtaining of in-vivo images from within body lumens or cavities, such as images of the gastrointestinal tract, where the data, such as mosaic image data, may typically be transmitted or otherwise sent to a receiving system in a compressed format. According to embodiments of the present invention, the mosaic data may be directly compressed, e.g. compressed without first completing and/or partially completing the RGB image data. According to other embodiments of the present invention, the compressed data may be transmitted on the fly.

BRIEF DESCRIPTION OF THE DRAWINGS

The present invention will be understood and appreciated more fully from the following detailed description taken in conjunction with the drawings in which:

FIG. 4 shows a transformation of mosaic data pixel arrangement from an [R, G1, G2, B] color space to an alternate color space according to an embodiment of the present invention;

Figure 1:
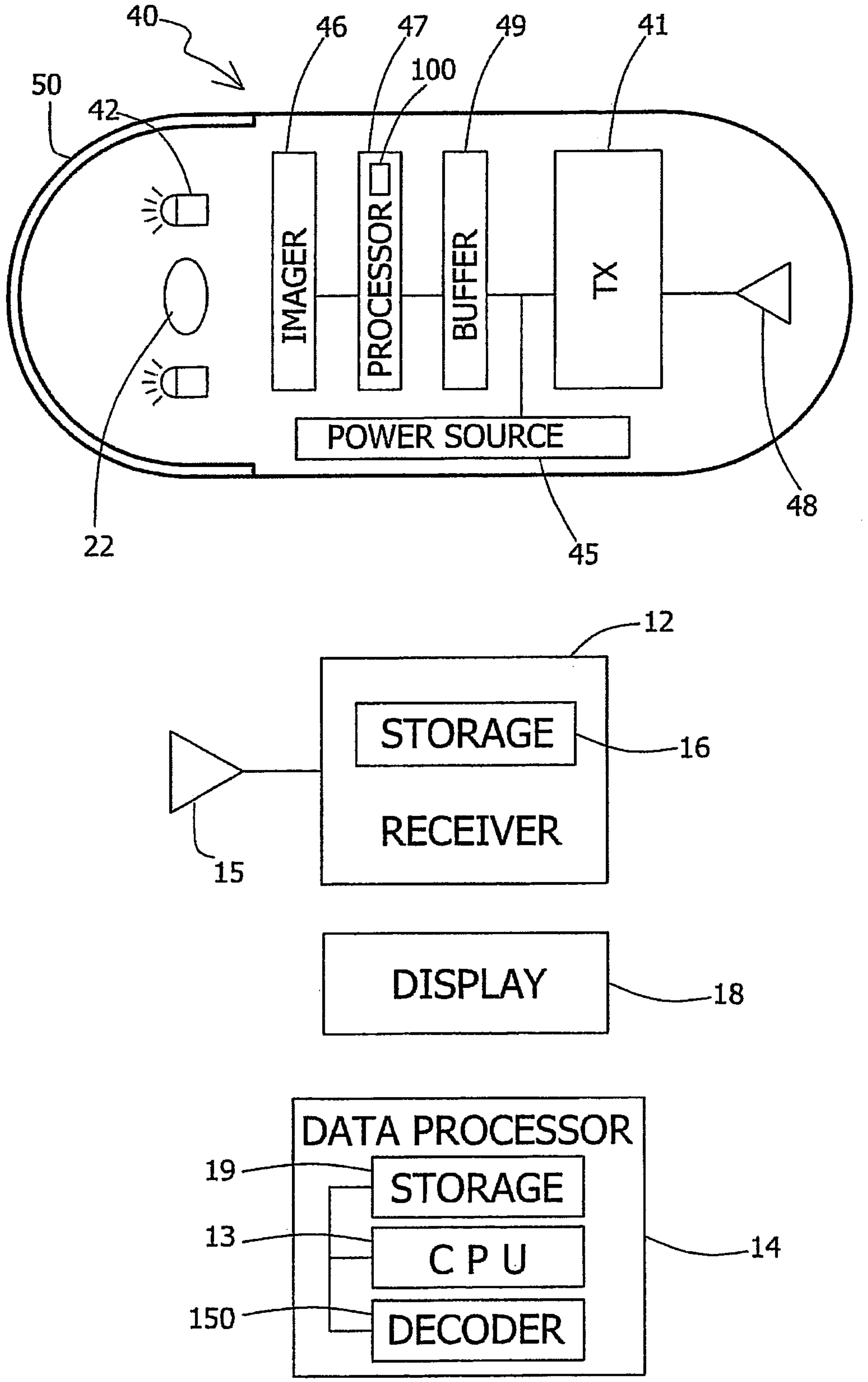
FIG. 1 shows a schematic diagram of an in-vivo imaging system according to embodiments of the present invention.

It will be appreciated that for simplicity and clarity of illustration, elements shown in the figures have not necessarily been drawn accurately or to scale. For example, the dimensions of some of the elements may be exaggerated relative to other elements for clarity, or several physical components may be included in one functional block or element Further, where considered appropriate, reference numerals may be repeated among the figures to indicate corresponding or analogous elements.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well-known features may be omitted or simplified in order not to obscure the present invention.

Embodiments of the system and method of the present invention may be used, for example, in conjunction with an imaging system or device such as may be described in U.S. Pat. No. 5,604,531 to Iddan et al. and/or in application number WO 01/65995 entitled "A Device And System For In Vivo Imaging", published on 13 Sep. 2001, both of which are hereby incorporated by reference. However, the device, system and method according to the present invention may be used with any device that may provide image and/or other data from within a body lumen or cavity. In alternate embodiments, the system and method of the present invention may be used with devices capturing information other than image information within the human body; for example, temperature, pressure or pH information, information on the location of the transmitting device, or other information.

Reference is made to FIG. 1, showing a schematic diagram of an in-vivo imaging system according to embodiments of the present invention. In an exemplary embodiment, a device 40 may be a swallowable capsule capturing images, for example, images of the gastrointestinal tract. Typically, device 40 may be an autonomous device and may include at least one sensor such as an imager 46, for capturing images, a processing chip or circuit 47 that may process signals generated by the imager 46, one or more illumination sources 42, an optical system 22, a transmitter 41 and a power source 45. In one embodiment of the present invention, the imager 46 may be and/or contain a CMOS imager. In other embodiments, other imagers may be used, e.g. a CCD imager or other imagers. In some embodiments of the present invention, the imager 46 may incorporate dark reference pixels that may enable the imager 46 to subtract dark pixels noise recorded intermittently between image capture using known methods. In other embodiments of the present invention, this feature may not be available. Processing chip 47 and or imager 46 may incorporate circuitry, firmware, and/or software for compressing images and/or other data, e.g. control data. In other embodiments, a compression module 100 and a buffer 49 may be incorporated either in the imager 46, processing chip 47, transmitter 41, and/or a separate component. In some embodiments of the present invention, the buffer 49 may have a capacity that may be substantially smaller than the size of a frame of image data captured, for example, from imager 46. Processing chip 47 need not be a separate component; for example, processing circuitry 47 may be integral to the imager 46, integral to a transmitter 41 and/or other suitable components of device 40. The buffer 49 may, for example, have a capacity of 0-20 kilobytes and may serve to facilitate, for example, a constant bit rate of data from the compression module 100 to the transmitter 41, Other uses of buffer 49 and/or other sizes of buffer 49 may be implemented. The transmitter 41 may, for example, transmit compressed data, for example, compressed image data and possibly other information (e.g. control information) to a receiving device, for example a receiver 12. The transmitter 41 may typically be an ultra low power radio frequency (RF) transmitter with high bandwidth input, possibly provided in chip scale packaging. The transmitter may transmit, for example, via an antenna 48. The transmitter 41 may, for example, include circuitry and functionality for controlling the device 40.

Typically, device 40 may be an autonomous wireless device that may be, for example, swallowed by a patient and may traverse a patient's GI tract. However, other body lumens or cavities may be imaged or examined with device 40. Device 40 may transmit image and possibly other data in a compressed format to, for example, components located outside the patient's body, which may, for example, receive and process, e.g. decode, the transmitted data. Preferably, located outside the patient's body in one or more locations, may be a receiver 12, preferably including an antenna or antenna array 15, for receiving image and possibly other data from device 40, a receiver storage unit 16, for storing image and other data, a data processor 14 with CPU 13, a data processor storage unit 19, a data decoding module 150 for decompressing data, and an image monitor and/or display 18, for displaying, inter alia, the images transmitted by the device 40 and recorded by the receiver 12. In one embodiment of the present invention, receiver 12 may be small and portable. In other embodiments receiver 12 may be integral to data processor 14 and antenna array 15 may be electrically communicated to receiver 12 by, for example, wireless connections. Other suitable configurations of receiver 12, antenna 15 and data processor 14 may be used. Preferably, data processor 14, data processor storage unit 19 and monitor 18 may be part of a personal computer, workstation, or a Personal Digital Assistant (PDA) device, or a device substantially similar to a PDA device. In alternate embodiments, the data reception and storage components may be of other suitable configurations. Further, image and other data may be received in other suitable manners and by other sets of suitable components.

Embodiments of the system and method of the present invention may provide transmission of compressed image data and possibly other data from, for example, in-vivo device 40. Compression as described herein may facilitate transmission of images at a higher frame rate without increasing, for example, the bandwidth of transmitter 41, may facilitate transmission with a lower bandwidth, and/or may facilitate increasing transmission gain per bit without increasing the overall energy required from the power source 45. Data other than or in addition to image data may be compressed and transmitted. For example, control information may be compressed. In-vivo autonomous devices, for example, device 40, may typically have limited space and power provision and therefore it may be desirable to minimize the processing power and buffer size and/or memory that may be required for compressing data. In some embodiments of the present invention, it may be desirable to accomplish compression of image and other data with memory capability.

Typically, the image data recorded and transmitted may be digital color image data although other image formats (e.g. black and white image data) may be used. In some embodiments of the present invention, each frame of uncompressed image data may include, for example, 256 rows of 256 pixels each, and each pixel may include data for color and brightness, according to known methods. In some embodiments of the present invention, the image data may be mosaic image data, for example, a pixel group, may be represented by a mosaic of for example four pixels, each pixel in the group may correspond to primaries such as red, green, and/or blue. One primary, e.g. green, may be represented twice. Other pixel arrangements and sizes may be used. Other sizes of pixel groups, including other numbers of pixels, may be used.

Reference is now made to FIG. 2 showing an exemplary mosaic pixel arrangement according to an embodiment of the present invention. In FIG. 2 every pixel group 250 may be represented by a mosaic of four pixels, for example, a red pixel 210, a blue pixel 220, a first green pixel 230, and a second green pixel 240. Corresponding pixel planes: red, blue, first green and second green planes according to the pixel arrangement shown in FIG. 2A are shown in FIG. 2B, 2C, 2D and 2E respectively. Known methods, e.g. known interpolation methods, may be used to create a complete Red, Green and Blue (RGB) pixel image that may include an RGB value in each of the pixel positions 299. A mosaic may include other numbers of pixels.

The data compression module 100 and decoder module 150 may use various data compression methods and systems. The data compression methods used may be lossless or lossy. Lossless data compression may enable precise (typically, with no distortion) decoding of the compressed data. The compression ratio of lossless methods may however be limited. Lossy compression methods may not enable precise decoding of the compressed information. However the compression ratio of lossy methods may typically be much higher than that of lossless methods, for example lossy compression may result in compression ratios greater than two. In many cases the data distortion of lossy methods may be non-significant and/or non-discernable with the human eye. Typically, known compression algorithms may compress or decrease the original size of the data by storing and/or transmitting only differences between one or more neighboring values, for example, pixels. In general, differences in color and intensity of images data may typically occur gradually over a number of pixels, and therefore the difference between neighboring pixels may be a smaller quantity as compared to the value of each pixel. In some embodiments of the present invention, a compression ratio of at least four may be desired.

Known, compression algorithms may include JPEG and/or MPEG compression that may typically be used for image and video compression and may have an option to operate according to either a lossless or lossy scheme. However such algorithms may typically require substantial processing power and memory, and may typically require full RGB data (as opposed to mosaic data) as input. Other known compression algorithms (that may typically be lossless), e.g., Binary Tree Predictive Coding (BTPC), Fast Efficient Lossless Image Compression System (FELICS), and Low Complexity Context-Based Lossless Image Compression Algorithm (LOCO-I), etc., may require relatively lower processing power and memory but may still require memory to, for example store tables and other data. In some embodiments of the present invention, known lossy and/or lossless methods may be revised and/or implemented with pre-processing of data to enable lossy compression to be implemented with reduced processing power and memory requirements, and to be compatible with mosaic image data input.

In some embodiments of the present invention, the performance of known compression algorithms may be improved by considering known characteristics of the system and the environment that may be imaged. In one example, the resolution of an image may be limited by, for example, optical system 22. Knowledge of the known limitations in the resolution may be, for example, incorporated into compression algorithms, e.g. by defining one or more parameters, so that higher performance may be achieved for the specific system being used. In other embodiments, a priori knowledge of the color scheme, or other characteristics of the image data may be incorporated in the compression algorithm. In other embodiments pre-processing may be implemented to increase performance of the compression algorithm. Performance may be based on compression ratio, processing, and/or memory requirement. Embodiments of the present invention describe a system and method for compression of image and other data at high compression rates, e.g. compression ratios of 4-8, with substantially little processing power and memory requirements.

Figure 2A:
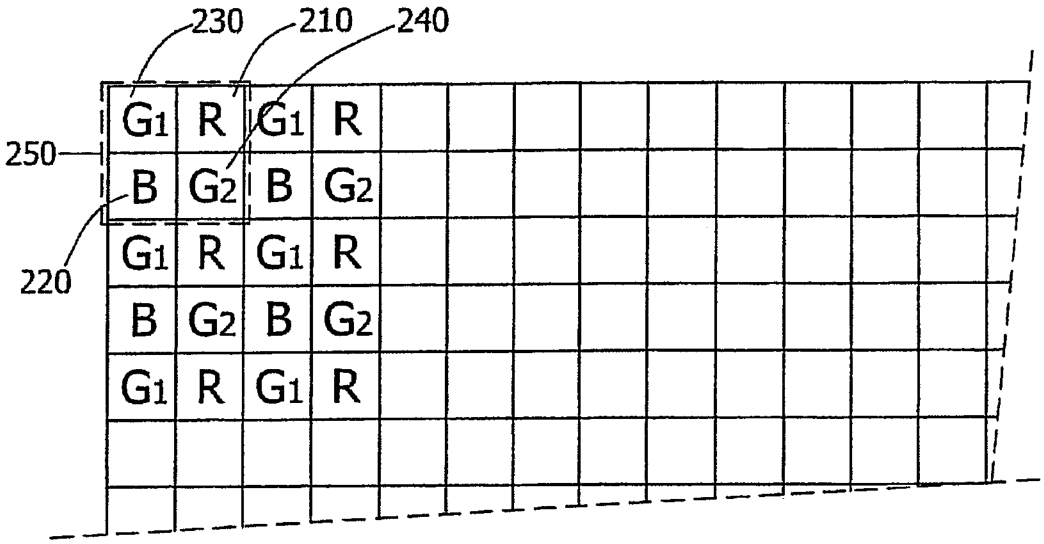
FIG. 2A shows an exemplary mosaic pixel arrangement according to embodiments of the present invention.
Figure 2B:
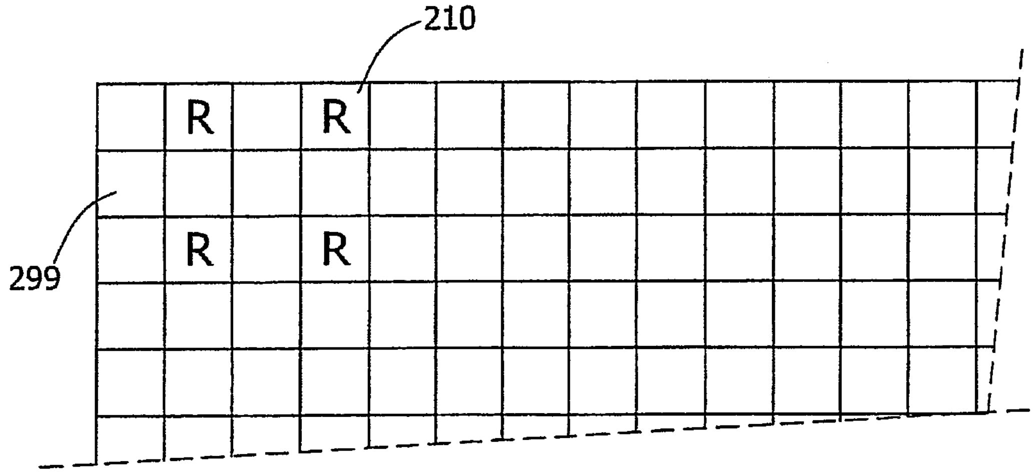
FIG. 2B shows an exemplary red pixel plane of a mosaic pixel arrangement according to embodiments of the present invention.
Figure 2C:
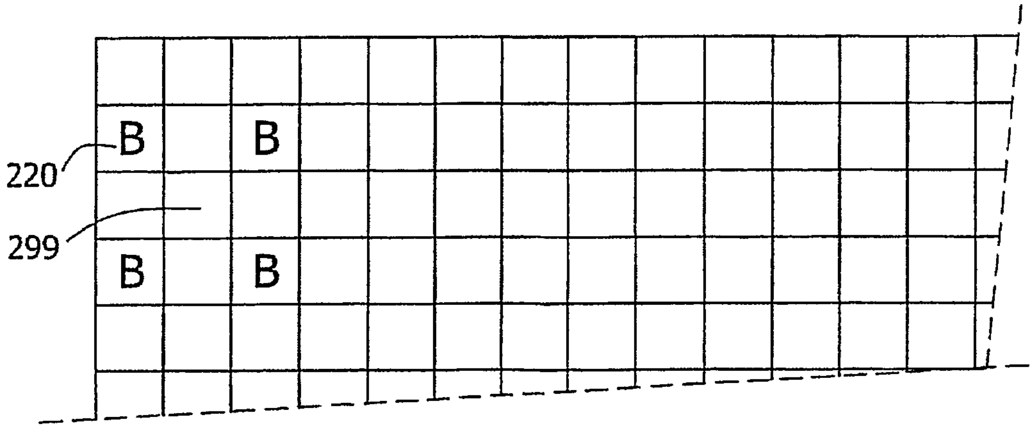
FIG. 2C shows an exemplary blue pixel plane of a mosaic pixel arrangement according to embodiments of the present invention.
Figure 2D:
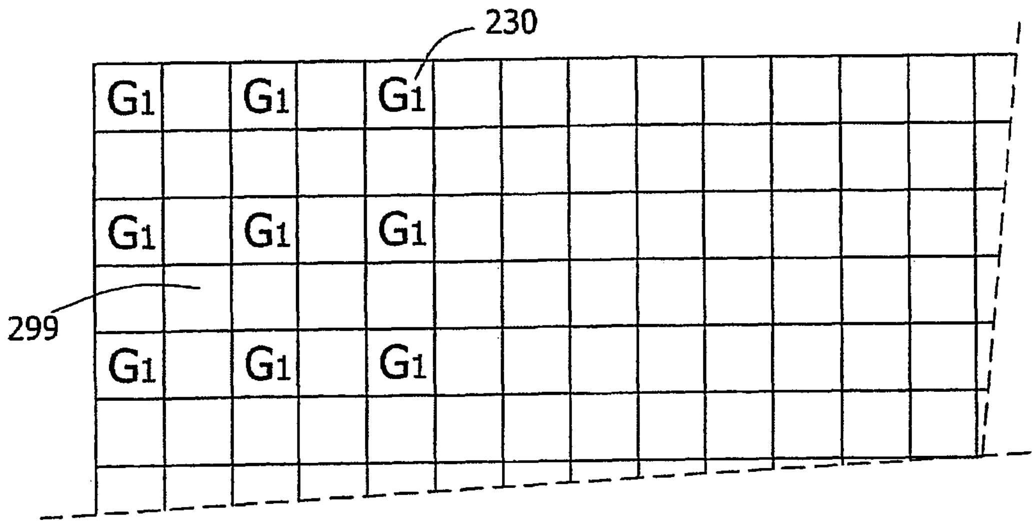
FIG. 2D shows an exemplary first green pixel plane of a mosaic pixel arrangement according embodiments of the present invention.
Figure 2E:
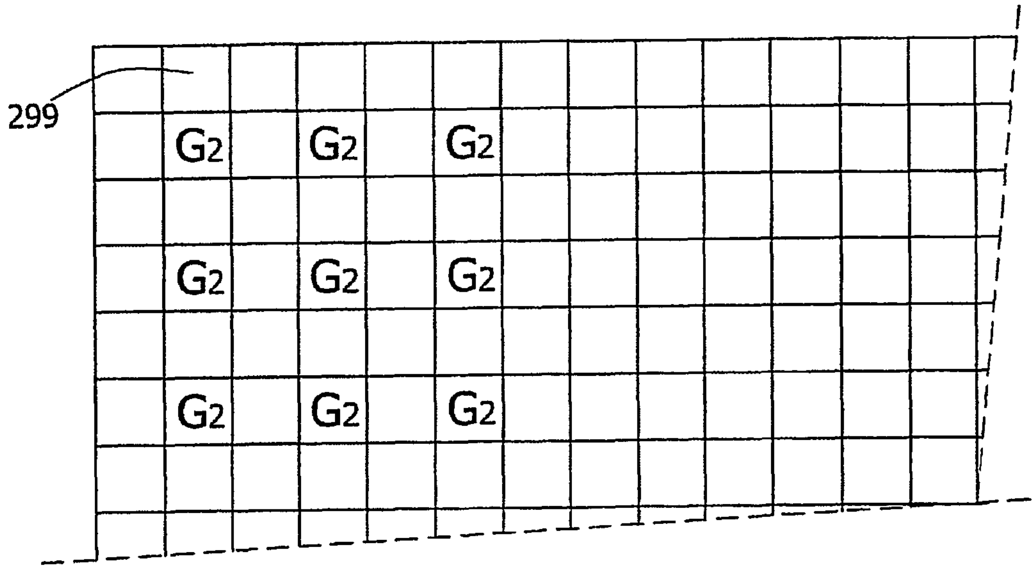
FIG. 2E shows an exemplary second green pixel plane of a mosaic pixel arrangement according to embodiments of the present invention.
Figure 3:
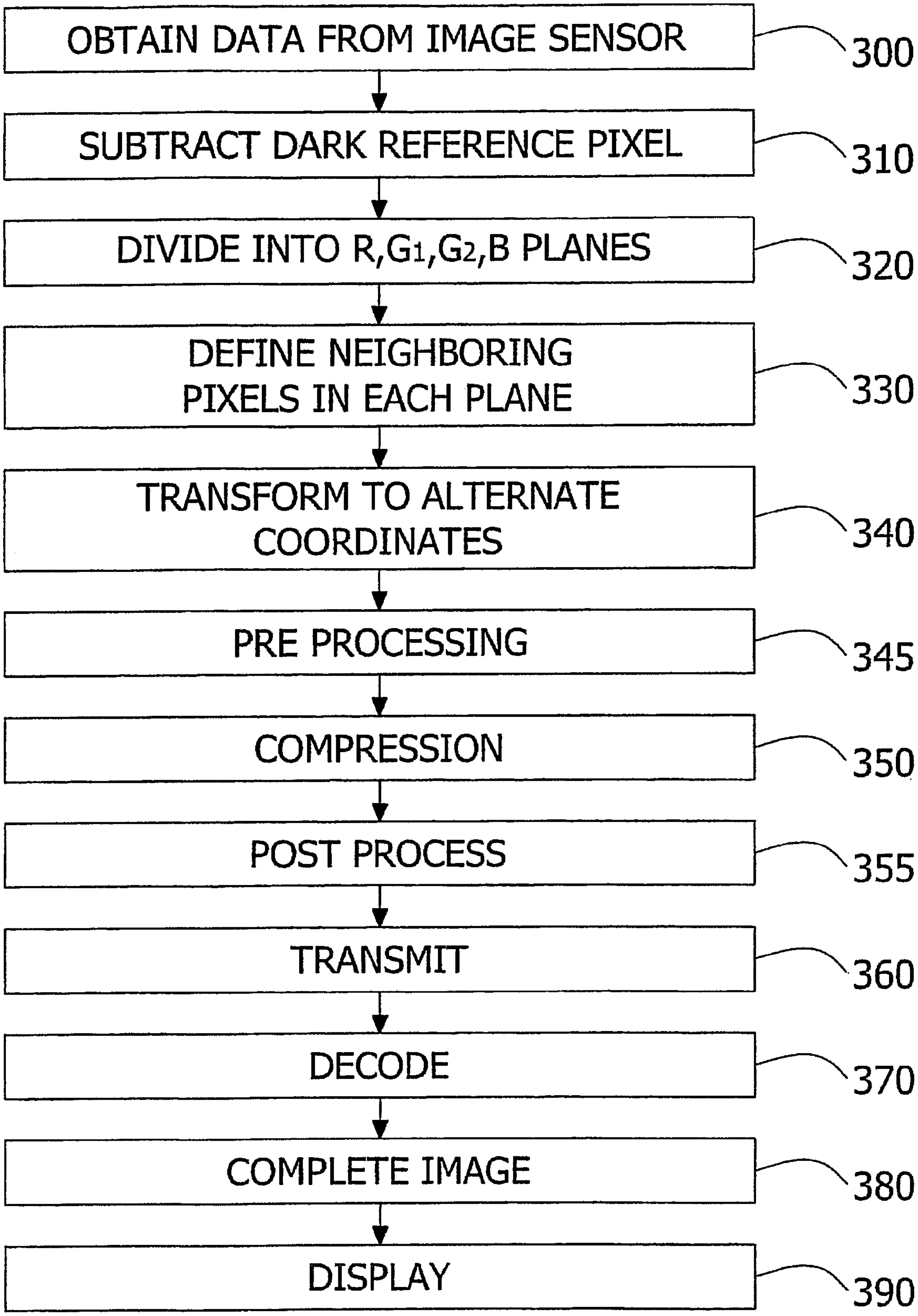
FIG. 3 shows a flow chart describing a method of compressing image data according to an embodiment of the present invention.

Reference is now made to FIG. 3 showing a method for compressing data according to one embodiment of the present invention. In block 300 image data may be obtained. In other embodiments data other than and/or in addition to image data may be obtained and compressed. Image data 300 may be mosaic image data, for example, as is shown in FIG. 2, complete RGB color image data, or other suitable formats of image data. Typically, for in-vivo devices, image data may be mosaic image data as may be described herein. In block 310 dark reference pixels may be subtracted from corresponding pixels. In other embodiments of the present invention, dark reference pixels may not be provided for each captured image. In some embodiments of the present invention, dark image information may be obtained using other known methods. For example, a dark image may be captured for a plurality of captured images. Subtraction of the dark image may be performed during or post decoding of the captured image using suitable methods. Dark images may be, for example, interpolated using suitable methods to estimate the dark image noise correspond to each of the captured images. In some embodiments of the present invention, compression and/or processing of data may result in shifting or distortion of image data. Compressing the dark images using similar steps and parameters as compression of the captured images may maintain the correspondence between the captured and dark images so that proper subtraction of dark image noise may be achieved. In block 320, the pixel plane may be divided, for example, into mono-color pixel planes, for example, planes shown in FIG. 2B-2E In one embodiment of the present invention, compression algorithms, for example, known predictive types of compression, may be performed on each of the mono-color pixel planes after filling the missing information on each of the planes. Other suitable compression algorithms besides known predictive type algorithms may be implemented. In some embodiments of the present invention, the mono-color plane may be filled using known algorithms, e.g. known interpolation methods to obtain data corresponding to a full RGB image. In some embodiments, compression may be performed directly on the mosaic plane (FIG. 2A) or the mono-color planes (FIG. 2B-2E) with out completing the RGB image. Known image compression algorithms, for example JPEG, may require a full RGB image before compression data. When applying this algorithm to mosaic image data, compression may require extra processing to fill and/or complete missing data as well as extra storing capability to store the larger size data. In some embodiments of the present invention, a compression method for directly compressing mosaic image data, e.g. data that is not full RGB data, without requiring a complete or substantially complete RGB image may be provided. In block 330 neighboring pixels required for pixel comparison may be defined and/or located (e.g. with pointers) as the closest pixels available having the same color. In block 340, a transformation may be performed to transform, for example, the RGB plane and/or coordinates (or [R, G1, G2, B] coordinates) of the image into alternate coordinates, according to embodiments of the present invention. Sample coordinates and/or dimensions may include, for example, Hue, Saturation, and Value [H, S, V] coordinates, [Y, I, Q] planes commonly used for television monitors, or [Y, U, V] commonly used in JPEG compression. In other embodiments, other dimensions and/or coordinates suitable for images captured in-vivo may be used, e.g. images of in-vivo tissues. In some embodiments of the invention, data may be a combination of image and non-image data, for example one or more dimensions of the data may represent non-image data.

Reference is now made to FIG. 4 showing an exemplary transformation according to an embodiment of the present invention using, for example, four coordinates, e.g. [Y, Cr, Cb, Gdiff], corresponding to, for example, the four pixels in the pixel group 250 shown in FIG. 2A. Other coordinates, transformations, and defined pixels and/or pixels groups may be used. Y may be, for example, representative of the intensity of an image, Cr may be, for example, representative of the color red, Cb may be, for example, representative of the color blue, and Gdiff may be, for example, representative of the difference between the first and second green pixels. Other transformations and/or other coordinates may be used in other embodiments of the present invention. Referring back to FIG. 3, pre-processing of data (block 345) may be performed, for example, one or more of the dimensions and/or coordinates may be discarded. Discarding a dimension may enable, for example, simplification of the computations subsequently required and/or reduction in the quantity of data to be handled and transmitted, e.g. increase the compression ratio. In block 350, a compression algorithm may be implemented. In some embodiments of the present invention, compression may be performed on the fly, for example, in units of a few lines at a time, e.g. four lines of pixels. In other examples, compression on the fly may be performed with more or less than four lines of pixels. Typically compression performed by compression module 100 may be based on a variety of known predictive codes, e.g. (BTPC, FELICS, LOCO-I) that may typically use information from, for example, two or more neighboring pixel, e.g. a pixel above and the pixel to the left. Other suitable methods of lossless and/or lossy compression may be implemented. To increase the performance of the compression algorithm used, e.g. increase the compression ratio; pre-processing (block 345) and/or post procession (block 355) of the data may be performed. For example, one or more Least Significant Bits (LSBs) in one or more dimension and/or parameters of the data may be discarded, e.g. during pre-processing, to increase the compression ratio in one or more dimensions of the data. In other examples, a priori knowledge of, for example, typical color may be implemented to, for example, emphasis and/or de-emphasis particular dimensions of an image. In yet other examples, a priori knowledge of the characteristics of the typical object imaged may be implemented to emphasis and/or de-emphasis details or local changes that may be known to or not to typically occur. For example, for imaging of in-vivo tissue, certain sharp changes in color may not be typical and if encountered in image data may, for example, be de-emphasized. In still yet other examples, a priori knowledge of the particular optical system used may be implemented to emphasize or de-emphasize details encountered. For example, if a sharp detail may be encountered and the optical system, for example optical system 22, may be known not to provide the capacity to discern such sharp details, this detail may be de-emphasized by for example discarding the LSB, performing smoothing, decimation, etc. Emphasis and/or de-emphasis may be implemented by, for example, pre-processing (prior to compression), post-processing, and/or defining parameters of the compression algorithm. In one embodiment of the present invention, one or more dimension of the image may, for example, be discarded. For example, if one or more of the dimension may be known to produce a relatively flat image in the environment being imaged, that dimension may, for example, be discarded and no computations may be performed in that dimension. This may serve to, for example, increase the compression ratio, decrease the memory required to perform compression, and simplify the coding so that less processing may be needed. In other embodiments of the present invention, processing required as well as the memory required for the coding may be reduced by, for example, customizing known algorithms, for example, by eliminating the adaptive part of the coding that may require large tables of accumulated data. By implemented a priori knowledge of typical images and/or data that may normally be captured with, for example, a particular sensing device capturing images, for example, in a particular environment, the adaptive part of the coding may be reduced to a minimum. Data other or in addition to image data may be compressed.

In block 360, compressed data may be transmitted. Compressed data as well as coding for the decoder and/or control data may be transmitted, for example in a compressed format. Due to compression each line may have a variable bit length. In some embodiments of the present invention, a buffer 49 may stall data until a predetermined quantity of data may be accumulated for transmission. In some embodiments of the present invention, a buffer 49 may temporarily stall data to adapt the output from the compression that may have a variable bit rate to a constant bit rate transmission. Transmission may be in portions substantially smaller than an image frame, for example, a portion may be one or more lines of data, e.g. 512 bits. Typically, entire images need not be stalled and/or stored. Data transmitted may be stored and subsequently decoded (block 370). In other embodiments of the present invention, decoding may be performed on the fly directly upon transmission. If dark reference pixels weren't subtracted during image capture, dark image information may be subtracted, for example, post decoding. The decoded mosaic image may be completed (block 380), e.g., by using known methods, e.g. known interpolation methods. The image may be display (390).

Typically, the data compression module 100 and decompression module 150 may include circuitry and/or software to perform data compression. For example, if the data compression module 100 or decompression module 150 are implemented as a computer on a chip or ASIC, data compression module 100 or decompression module 150 may include a processor operating on firmware which includes instructions for a data compression algorithm. If data decompression module 150 may be implemented as part of data processor 14 and/or CPU. 13, the decompression may be implemented as part of a software program. Other suitable methods or elements may be implemented.

In some embodiments of the present invention, the rate of transmission may be, for example, approximately 1.35 Megabits per second. Other suitable rates may be implemented. Compression may significantly reduce the rate of transmission required or significantly increase the quantity of information that may be transmitted at this rate. After compression, and before transmission, randomization may occur (performed, for example, by the transmitter 41). Namely, the occurrence of the digital signals ("0" and "1") may be randomized so that transmission may not, for example, be impeded by a recurring signal of one type. In some embodiments of the present invention, an Error Correction Code (ECC) may be implemented before transmission of data to protect the data transmitted, for example, Bose Chaudhuri Hocquenghem (BCH) may be used.

Figure 5:
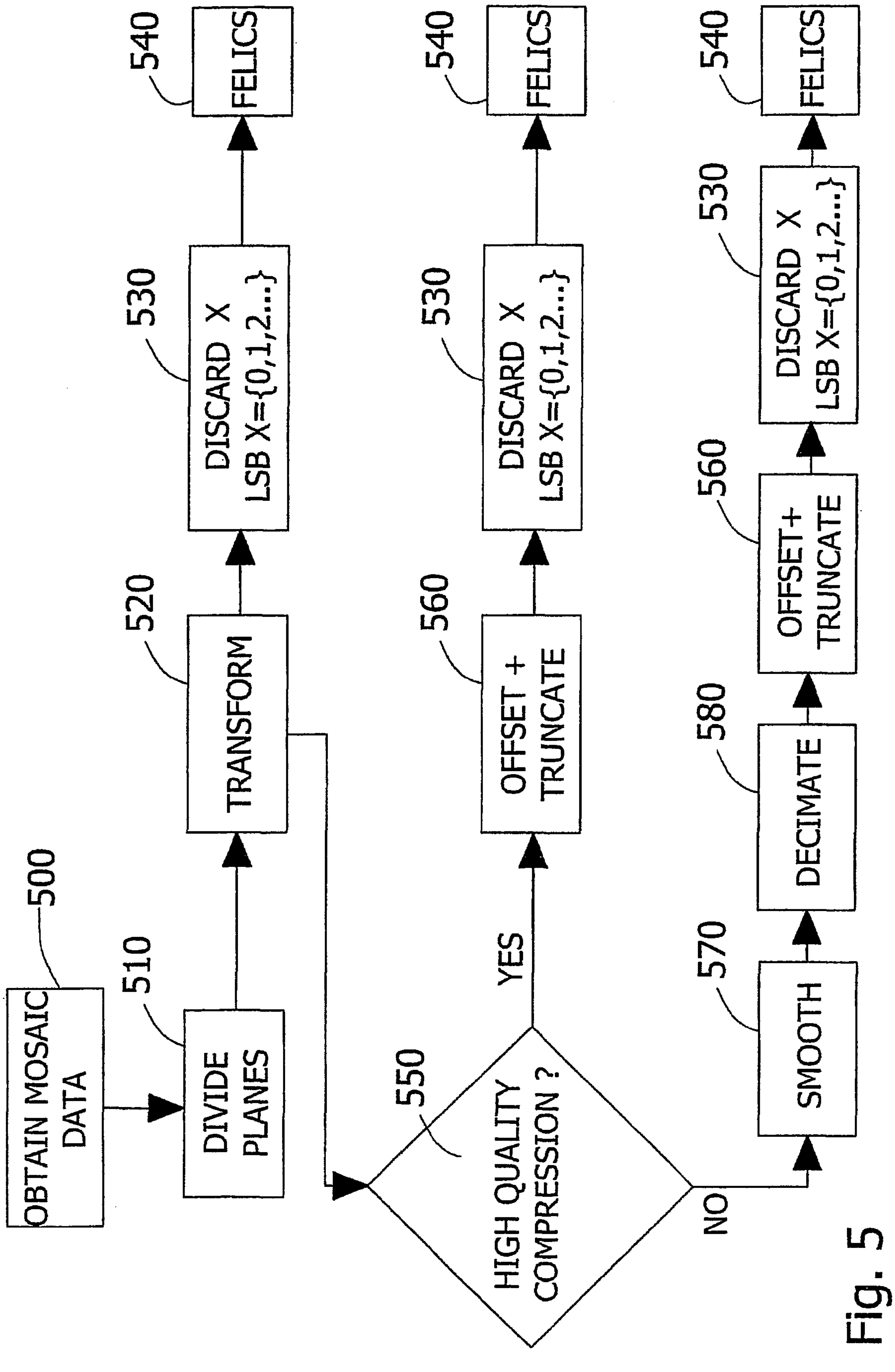
FIG. 5 shows a flow chart describing a method of compressing image data according to other embodiments of the present invention.

Reference is now made to FIG. 5 showing a flow chart describing a method of compression for in-vivo data according to other embodiments of the present invention. In block 500 data, e.g. mosaic type data may be obtained. The mosaic type data may be, for example, a 256×256 pixel image. Other size data and data other than image data may be used, for example, a 512×512 pixel image may be obtained. In block 510 the mosaic image may be divided into its separate planes, for example four separate planes. The planes may be separated as shown in FIG. 2B-2E according to the pixel arrangement shown in FIG. 2A. Other pixels arrangement may be used, for example, a mosaic pixel arrangement with two blue pixels for every red and green pixel or two red pixels for every blue and green pixel, or other colors may be included in the pixel arrangement. In other examples, there may be other pixel arrangements based on more or less than four pixels. Planes may not be actually separated, instead pointers may be defined or reference may be noted of where the pixels with the same colors may be located. In block 520 a transformation may be implemented to transform, for example, the four planes to other dimensions and/or coordinates. In one embodiment of the present invention an exemplary transformation shown in FIG. 4 may be used. In other embodiments of the present invention, other dimensions may be defined and/or used, for example, one of the dimensions described herein or other known dimensions. In yet other embodiments of the present inventions, transformation need not be implemented, for example, compression may be performed on the original coordinates. In FIG. 4 the Y dimension may be representative of the intensity and in some embodiments may be regarded as containing a large part of the information. As such the pre-processing the data in, for example, the Y dimension may be different from the other dimensions present. One of the methods that may be implemented to decrease the size of the data may be to discard one or more LSB(s), for example one LSB, as is shown in block 530. Other suitable methods may be employed to decrease the size of the data e.g. increase the resultant compression ratio. In one embodiment of the present invention, the Y dimension may be further compressed using known lossless compression algorithms, for example, FELICS (block 540). Other suitable compression algorithms may be used. In one embodiment of the present invention, for one or more of the other dimensions, a decision (block 550) may be made to determine the pre-processing to be implemented. In one example, the decisions may be based on the current size data stalled in the buffer 49, or based on other parameters, or may be predetermined. In one example, if the decision is to compress while maintaining high quality data, the data may be compressed and/or preprocessed less aggressively, e.g. resulting in a lower compression ratio. For high quality data compression, the data may, for example, be offset as in block 560, one or more LSB(s) may be discarded and the data may be compressed using any known compression algorithms, for example, FELICS (block 540). Other compression algorithms may be implemented. For lower quality data compression, the data may, for example, first be smoothed (block 570) using known methods. In one example, a smoothing filter with a 2×2 window may be implemented. In other examples other smoothing methods may be used. Subsequent to smoothing the data may be decimated (block 580) to reduce the size. For example, decimation may be used to reduce data that in one dimension that may be originally 128×128 bytes to, for example, 64×64 bytes. In other examples, the data may be decimated to other suitable sizes. In block 560 data may be offset and truncated. One or more LSB(s) may be discarded (block 530) to decrease the size of the data before implementing a compression algorithm for example, FELICS. In other embodiments of the present invention, one or more blocks may not be implemented. For example, one or more of blocks 530, 560, 570, 580 may or may not be implemented. In other embodiments, other pre-processing may be implemented. In some embodiments of the present invention it may be desired to further reduce the processing power required to compress transmitted data. In one example, one or more of the dimensions defined by transform (520) may be discarded. Discarding a dimension of the defined data may serve to reduce the processing power required for compression and may increase the resultant compression ratio. In one example, the dimension defined by Gdiff may be, for example, discarded. In other examples, other dimensions or more than one dimension may be discarded. Other methods of increasing compression ratio, decreasing required processing power, and/or decreasing required memory capacity may be implemented.

Known compression algorithms, for example FELICS, may require tables of accumulated data to define parameters that may, for example, be used to adapt tie algorithm to, for example, selecting the optimal parameter for Golomb and Rice codes thus having minimal length compressed data. Sustaining tables of accumulated data may require memory to store the tables of accumulated data as well as extra processing power to define the required adaptation, e.g. compute the required parameter. In some embodiments of the present invention, known compression algorithms may be revised to due away with tables of accumulated data. In one embodiment of the present invention, constant values for parameters that may be otherwise determined based on one or more tables of accumulated data, e.g. two-dimensional array of data may be defined. The predetermined value of the parameter may be based on, for example, a priori information on the quality of the data expected due to the optical system used, due to the characteristics of the objects being imaged, for example, color, level of detail, etc. Other considerations may be used to define the parameters. In one embodiment of the present invention, when implementing a FELICS algorithm, the known parameter K in Golomb and Rice codes may be defined, for example, as K=1 for the Y dimension, and K=0 for other dimensions. Other suitable values of K for one or more dimensions may be defined. In other embodiments of the present invention, tables of accumulated data may be used but limited to a predetermined size so as to limit the memory and the processing required.

Compressed data may be transmitted to, for example, an external receiver 12, in portions. Compressed data that may be of variable size may pass through a buffer 49 before transmission. Once the portion defined for transmission is filled, data accommodated in the buffer 49 may be transmitted. The data size of the defined portions may be the size of one or more images or may be the size of a few lines of data. The buffer 49 may provide for use of a constant bit rate transmitter for transmitting data of variable size. In one embodiment of the invention, compression data may be transmitted on the fly by transmitting portions equaling, for example, approximately two lines of pixel data while the buffer size may be in the order of magnitude of, for example, four lines of pixel data. Other suitable buffer sizes and transmission portions may be used. In some embodiments of the present invention, overflowing of the buffer 49 may be avoided by implementing a feed back mechanism between the buffer 49 and the compression algorithm. The feedback mechanism may control the compression ratio of the algorithm based on the rate that the buffer 49 may be filling up. Other methods of transmitting and using buffers may be implemented.

Data transmitted may be received by an external receiver, for example receiver 12. Decoding and/or decompression may be performed on receiver 12 or on data processor 14 where data from the receiver may be subsequently downloaded. In exemplary embodiment data decompression module 150 may be a microprocessor or other micro-computing device and may be part of the receiver 12. In alternate embodiments the functions of the data decompression (decoding) module 150 may be taken up by other structures and may be disposed in different parts of the system; for example, data decompression module 150 may be implemented in software and/or be part of data processor 14. The receiver 12 may receive compressed data without decompressing the data and store the compressed data in the receiver storage unit 16. The data may be later decompressed by, for example data processor 14.

Preferably, compression module 100 may be integral to imager 46. In other embodiments of the present invention, the data compression module 100 may be external to the imager 46 and interface with the transmitter 41 to receive and compress image data; other units may provide other data to data compression module 100. In addition, the data compression module 100 may provide the transmitter 41 with information such as, for example, start or stop time for the transfer of image data from the data compression module 100 to the transmitter 41, the length or size of each block of such image data, and the rate of frame data transfer. The interface between the data compression module 100 and the transmitter 41 may be handled, for example, by the data compression module 100.

In alternate embodiments, tile data exchanged between the data compression module 100 and the transmitter 41 may be different, and in different forms. For example, size information need not be transferred. Furthermore, in embodiments having alternate arrangements of components, the interface and protocol between the various components may also differ. For example, in an embodiment where a data compression capability is included in the transmitter 41 and the imager 46 may transfer un-compressed data to the transmitter 41, no start/stop or size information may be transferred.

Figure 6:
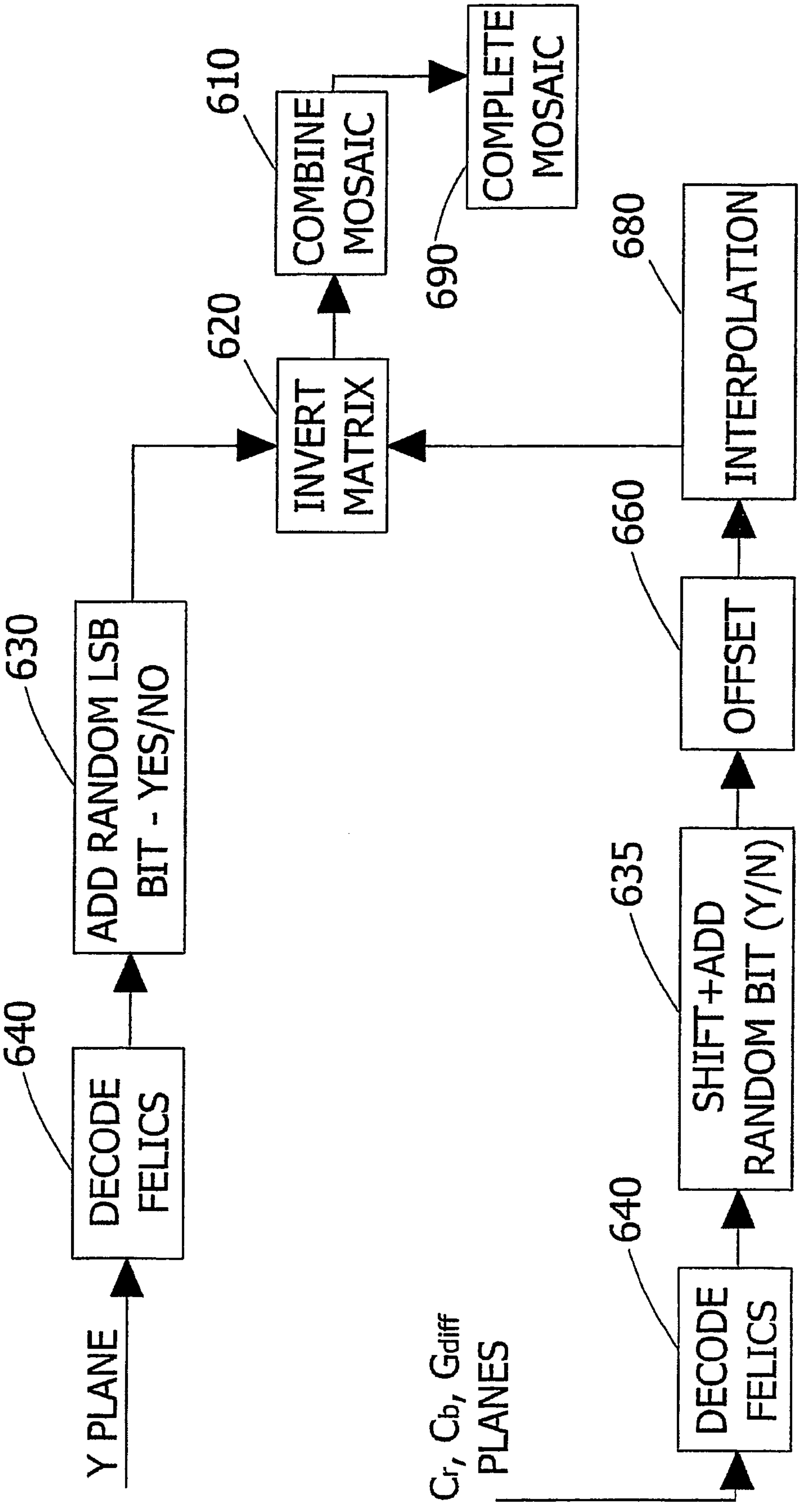
FIG. 6 shows a flow chart describing a decoding method for decoding compressed data according to an embodiment of the present invention.

Reference is now made to FIG. 6. Typically the method of decoding compressed data may be based on the method of compression, by generally reversing the steps taken for compression of the data, and pre-processing and/or post-processing of the data. For example, when using FELICS compression, the known decoding of FELICS may be implemented to decode the compressed data (block 640). For decoding of the Y plane and/or dimension described in FIG. 5, one or more random bit(s) of noise may be added (block 630) to replace the previously discarded one or more LSB(s). The random bits may be generated by any of the known algorithms for generating random bits. In some embodiments of the present invention known pseudo-random bits may be used, for example, pseudo-random noise quantization using a dithering method. Other methods of producing pseudo-random bits may be used. In still other embodiments of the present invention bits generated from a suitable algorithm may be used. Decoding of the other dimensions and/or planes, e.g. [Cr, Cb, Gdiff], may be accomplished in a similar manner. Decoding based on the implemented compression algorithm, for example FELICS (block 640), may be performed on each of the dimensions. Any LSBs that may have been discarded may be replaced (block 635) as described herein. Offsetting may be reversed (block 660) and interpolation (block 680), for example, linear interpolation may be performed to restore, for example, decimated data to their original size. In other embodiments of the present invention, one or more of the planes, e.g. Gdiff, may not be used, e.g. transmitted, and as such not decoded. In block 620, the data from all the dimensions may be transformed to, for example, their original coordinates, for example to RG1*G*2B coordinates. In block 610 the image may be restored, e.g. the individual color panes may be combined onto one plane (FIG. 2A), and filled (block 690) to a true RGB image by known interpolation and/or other suitable methods so that for example, there may be an RGB value for each pixel. Compression and decoding of the mosaic image as opposed to the true RGB image may serve to minimize and/or reduce the processing power, rate, and memory required to compress image data. Subsequent to decoding, dark reference image frames may be subtracted from corresponding images if required.

Embodiments of the present invention may include apparatuses for performing the operations herein. Such apparatuses may be specially constructed for the desired purposes (e.g., a “computer on a chip” or an ASIC), or may comprise general purpose computers selectively activated or reconfigured by a computer program stored in the computers. Such computer programs may be stored in a computer readable storage medium, such as, but is not limited to, any type of disk including floppy disks, optical disks, CD-ROMs, magnetic-optical disks, read-only memories (ROMs), random access memories (RAMs), electrically programmable read-only memories (EPROMs), electrically erasable and programmable read only memories (EEPROMs), magnetic or optical cards, or any other type of media suitable for storing electronic instructions.

The processes presented herein are not inherently related to any particular computer or other apparatus. Various general-purpose systems may be used with programs in accordance with the teachings herein, or it may prove convenient to construct a more specialized apparatus to perform the desired method. The desired structure for a variety of these systems appears from the description herein. In addition, embodiments of the present invention are not described with reference to any particular programming language. It will be appreciated that a variety of programming languages may be used to implement the teachings of the invention as described herein.

Unless specifically stated otherwise, as apparent from the discussions herein, it is appreciated that throughout the specification discussions utilizing terms such as “processing”, “computing”, “calculating”, “determining”, or the like, typically refer to the action and/or processes of a computer or computing system, or similar electronic computing device (e g., a “computer on a chip” or ASIC), that manipulate and/or transform data represented as physical, such as electronic, quantities within the computing system’s registers and/or memories into other data similarly represented as physical quantities within the computing system’s memories, registers or other such information storage, transmission or display devices.

It will be appreciated by persons skilled in the art that the present invention is not limited to what has been particularly shown and described hereinabove. Rather the scope of the present invention is defined only by the claims, which follow:

The invention claimed is:

1. A method for transmitting in-vivo data comprising:
- obtaining mosaic image data in a first set of coordinates comprising a plurality of colors wherein each color defines a plane of the image data;
- defining a location of neighboring pixels for each plane;
- transforming, using a processor, each plane of the image data to an alternate plane in a second set of coordinates;
- selecting a compression ratio to be used;
- preprocessing each alternate plane by discarding a least significant bit of the transformed data, to increase a compression ratio;
- if a high compression ratio is selected, further preprocessing the data by smoothing and decimating;
- compressing each alternate plane of the image data subsequent to preprocessing;
- storing the compressed image data in a buffer; and
- transmitting the compressed image data.

2. The method according to claim 1 wherein the first set of coordinates comprises: [R, G1, G2, B].

3. The method according to claim 1 wherein the second set of coordinates comprises [Y, Cr, Cb, Gdiff].

4. The method according to claim 1 wherein defining the location of neighboring pixels is by defining pointers.

5. The method according to claim 1 wherein compressing is by FELICS.

6. The method according to claim 1 further comprising:
- determining a second pre-process to perform on a plane of the image data before compression.

7. The method according to claim 6 wherein said second pre-process performed on the image data is selected from a group consisting of: smoothing, decimating, and offsetting and truncating.

8. The method according to claim 6 wherein the pre-process is determined for each image based on current size of data stalled in the buffer.

9. The method according to claim 6 wherein the pre-process is predetermined for each plane in the second set of coordinates.

10. The method according to claim 1 comprising subtracting a reference dark pixel from a corresponding pixel.

11. The method according to claim 1 wherein the transmitting is by constant bit rate.

12. The method according to claim 1 wherein said preprocessing comprises discarding one or more coordinates of the alternate plane of the image data.

13. The method according to claim 1 wherein said preprocessing comprises discarding two or more Least Significant Bits (LSBs) of the image data.

14. The method according to claim 1 comprising controlling the compression ratio based on a rate that the buffer is filling up.

* * * * *